United States Patent
Hsieh et al.

(10) Patent No.: US 9,200,270 B2
(45) Date of Patent: Dec. 1, 2015

(54) METHODS FOR TRANSFORMING YEAST

(75) Inventors: Chung-ming Hsieh, Newton, MA (US); Jonathan P. Belk, Grantham, NH (US); Jennifer M. Perez, Worcester, MA (US); Lorenzo Benatuil, Medford, MA (US)

(73) Assignee: AbbVie Inc., North Chicago, IL (US)

( * ) Notice: Subject to any disclaimer, the term of this patent is extended or adjusted under 35 U.S.C. 154(b) by 554 days.

(21) Appl. No.: 12/380,703

(22) Filed: Mar. 3, 2009

(65) Prior Publication Data
US 2009/0264320 A1    Oct. 22, 2009

Related U.S. Application Data

(60) Provisional application No. 61/067,910, filed on Mar. 3, 2008.

(51) Int. Cl.
| C12N 1/16 | (2006.01) |
|---|---|
| C12N 1/18 | (2006.01) |
| C12N 15/87 | (2006.01) |
| C12N 13/00 | (2006.01) |
| C12N 15/13 | (2006.01) |

(52) U.S. Cl.
CPC .............. *C12N 13/00* (2013.01); *C12N 15/87* (2013.01); *C12N 1/16* (2013.01); *C12N 1/18* (2013.01)

(58) Field of Classification Search
CPC ............ C12N 1/16; C12N 1/18; C12N 15/87; C12N 13/00
See application file for complete search history.

(56) References Cited

U.S. PATENT DOCUMENTS

| 4,808,537 A | 2/1989 | Stroman et al. |
|---|---|---|
| 4,837,148 A | 6/1989 | Cregg |
| 4,855,231 A | 8/1989 | Stroman et al. |
| 4,879,231 A | 11/1989 | Stroman et al. |
| 4,882,279 A | 11/1989 | Cregg |
| 4,929,555 A | 5/1990 | Cregg et al. |
| 5,135,868 A | 8/1992 | Cregg |
| 5,212,087 A | 5/1993 | Fournier et al. |
| 5,231,007 A | 7/1993 | Heefner et al. |
| 5,268,273 A | 12/1993 | Buckholz |
| 5,665,600 A | 9/1997 | Hagenson et al. |
| 5,716,808 A | 2/1998 | Raymond |
| 5,736,383 A | 4/1998 | Raymond |
| 7,009,045 B2 | 3/2006 | Abbas et al. |
| 2006/0019287 A1* | 1/2006 | Baker et al. ................. 435/6 |

OTHER PUBLICATIONS

Mapp Lab protocol, Mar. 18, 2005.*
Thompson et al., "An Improved Protocol for the Preparation of Yeast Cells for Transformation by Electroporation", 1998, Yeast, 14:565-571.*
Chao et al., "Isolating and Engineering Human Antibodies Using Yeast Surface Display", 2006, Nat. Protocols, 1(2):755-768.*
Neumann et al., "Calcium-Mediated DNA Adsorption to Yeast Cells and Kinetics of Cell Transformation by Electroporation", 1996, Biophys. J., 71:868-877.*
Sanchez et al., "Transformation of Kluyveromyces lactis by Electroporation", 1993, Applied and Environmental Microbiology, pp. 2087-2092.*
Gallie (Electroporation Protocols for Microorganisms, Methods in Molecular Biology, vol. 47, 1995, pp. 81-91).*

(Continued)

*Primary Examiner* — Jeremy C Flinders
(74) *Attorney, Agent, or Firm* — Lathrop & Gage LLP; James H. Velema, Esq.

(57) ABSTRACT

This invention is directed to the transformation of yeast, and mutants thereof, by electroporation, which result in stably transformed yeast host cells that express recombinant products. This invention also is directed to transformed yeast cells and libraries.

15 Claims, 3 Drawing Sheets

(56) References Cited

OTHER PUBLICATIONS

Kurtzman et al. (Topics in Current Genetics, 2005, 15:29-46).*
Meilhoc et al. (Bio/Technology, 1990, 8:223-227).*
Wu et al. (BioTechniques, 2004, 36:152-154).*
Wang et al. (J. Microbiol., 2011, 49:469-472).*
Chen et al. (Microbiol. Res., 2008, 163:531-537).*
Tekle et al. (Proc. Natl. Acad. Sci., 1991, 88:4230-4234.*
Fologea et al. (Bioelectrochemistry and Bioenergetics, 1998, 46:285-287).*
Lee, Hae-Won, Construction and characterization of a pseudo-immune human antibody . . . , Biochemical and Biophysical Research Communications, 2006, p. 896-903, vol. 346.
Liauta-Teglivets, O., et al., Molecular Cloning of the GTP-Cyclohydrolase Structural Gene RIBI of Pichia guilliermondii . . . , Yeast, 1995, p. 945-952, vol. 11.
Lipovsek, Dasa, Evolution of an Interloop Disulfide Bond in High-Affinity Antibody Mimcs Based on Bibronectin . . . , J. of Molecular Biology, 2007, p. 1024-1041, vol. 368.
Meilhoc, Elaine et al., High Efficiency Transformation of Intact Yeast Cells by Electric Field Pulses, Nature Biotechnology, 1990, p. 223-227, vol. 8.
Neumann, E. et al., Calcium-Mediated DNA Adsoption to Yeast Cells and Kinetics of Cell Transformation by Electroporation, Biophysical Journal, 1996, p. 868-877, vol. 71.
Piredda, Sandrine et al., Development of a Transformation System for the Yeast Yamadazyma (Pichia) Ohmeri, Yeast, 1994, p. 1601-1612, vol. 10.
Pla, Jesus et al., Cloning of the Candida Albicans H1S1 gene by direct comoplementation of a C. Albicans histidine auxotroph using . . . , Gene, p. 115-120, vol. 165(1).
Rothe, Christine et al., The Human Combinatorial Antibody Library HuCAL Gold Combines Diversification . . . , Journal of Molecular Biology, 2008, p. 1182-1200, vol. 376.
Sblattero, Daniel et al., Exploiting recombination in Single bacteria to make large phage antibody libraries, Nature Biotechnology, 2000, p. 75-80, vol. 18.
Sblattero, Daniel et al., A definitive set of olingonucleotide primers for amplifying human V regions, Immunotechnology, 1998, p. 271-278, vol. 3.
Griffiths, Andrew D. et al, Isolation of high affinity human antibodies directly from large synthetic repertoires, The EMBO Journal, 1994, p. 3245-3260, vol. 13(14).
He, Mingyue et al., Ribosome display: next-generation display technologies for prodcution of antibodies in vitro, Exper Rev. Proteomics, 2005, p. 421-430, vol. 2.
Helmuth, Martin et al, An electrotransfection Protocol for Yeast Two-Hybrid Library Screening, Analytical Biochemistry, 2001, p. 149-152, vol. 293.
Hoet, Rene Michael et al, Generation of high-affinity human antibodies by combining donor-derived and synthetic . . . , Nature Biotechnology, 2005, p. 344-348, vol. 23.
Hoogenboom, Hennie R., Overview of Antibody Phage-Display Technology and Its Applications, Methods in Molecular Biology, 2002, p. 1-37, vol. 178.
Hoogenboom, Hennie R., Selecting and screening recombinant antibody libraries, Nature Biotechnology, 2005, p. 1105-1116, vol. 23.
Kasuske, Anette et al., Efficient Electropulse, Transformation of Intact Candida Maltosa Cells by Different Homologous Vectore Plasmids, Yeast, p. 691-697, vol. 8.
Kunze, G. et al, Trasnformation of the industrially important yeasts Candida maltosa and Pichia guilliermondii, J. Basic Microbiology, 1985, p. 141-144, vol. 25(2).
Kuzne, G. et al., Transformation of Candida maltosa and Pichia guilliermondii by a plasmid containing saccharomyces . . . , Current Genetics, 1985, p. 205-209, vol. 9.
Kunze, G. et al., Transformations of the Industrially Important Yeast Candida Maltosa and Pichia guilliermondii, Acta Biotechnology, 1986, p. 28, vol. 6(1).

Scorer, Carol et al., Rapid Selection using G418 of High Copy Number Transformants fo Pichia pastoris . . . , Nature Biotechnology, 1994, p. 181-184, vol. 12.
Segal, Liat et al., Nucleotide variation of regulatory motifs may lead to distinct expression patterns, Bioinformatics, 2007, p. i440-i449, vol. 27.
Sherman, Fred, Laboratory Course Manual of Methods in yeast Genetics, Cold Spring Harbor Laboratory, 1986, p. 91-102.
Simon, John R., Transformation of Intact Yeast Cells by Electroporation, Methods in Enzymology, 1993, p. 487-483, vol. 271.
Struhl, Kevin et al., High-frequency transformation of yeast: Autonomous replication of hybrid DNA molecules, Proc. Natl. Acad. Sci., 1979, p. 1035-1039, vol. 76(3).
Suga, Minory et al., High-efficiency electroporation by freezing intact yeast cells with addition of calcium, Curr. Genet., 2003, p. 206-211, vol. 43.
Takagi, Masamichi et al., Construction of a Host-Vector System in Candida Maltosa by Using an ARS . . . , Journal of Bacteriology, 1986, p. 551-555, vol. 167.
Thompson, J.R. et al., An Improved Protocol for the Preparation of Yeast Cells for Transformation by . . . , Yeast Functional Analysis Report, 1998, p. 565-571, vol. 14.
Weaver, James C. et al., Electroporation high frequency of occurrence of a transient high . . . , Federation of European Biochemical Societies, 1988, p. 30-34, vol. 229(1).
Yang, Vina W. et al., HIgh-Efficiency Transformation of Pichia Stipitis Based on its URA3 Gene and a Homologous . . . , Applied and Environmental Microbiology, 1994, p. 4245-4254.
Becker, Daniel et al, High Efficiency Transformation of Yeast by Electroporation, Methods in Enzymology, 1991, p. 182-187; vol. 194.
Brzobohaty, Bretislav et al, Factors Enhancing Genetic Transofmration fo Intact Yeast Cells Modify Cells . . . , Journal of General Microbiology, 1986, p. 3089-93; vol. 132.
Cannon, Richard D. et al, Isolation and neclotide sequence of an automonomously replicating sequence (ARS) element functional . . . Mol. Gen. Genet., 1990, p. 210-218, vol. 221.
Chao, Ginger et al, Isolating and engineering human antibodies using yeast surface display, Nature Protocols, 2006, p. 755-768, vol. 1.
Clyne, Rosemary K. et al, Genetic Analysis of an ARS element from the fission yeast Schizosaccaromyces pombe, The EMBO Journal, 1995, p. 6348-6357, vol. 14(23).
Colby, David et al, Engineering Antibody Affinity by Yeast Surface Display, Methods in Enzymology, 2004, vol. 388, p. 351-351.
Faber, Klaas Nico et al, Highly-efficient electrotransformation fo the yeast Hansenula polymorpha, Current Genetics, 1994, p. 305-310, vol. 25.
Feldhaus, Michael J. et al, Flow-cytometric isolation of human antibodies from a nonimmune Saccharomyces cerevisiae . . . , Nature Biotechnology, 2003, p. 163-170, vol. 21.
Gai, S. Annie et al, Yeast surface display for protein engineering and characterization, Current Opinion in Structural Biology, 2007, p. 467-473, vol. 17.
Gietz, R. Daniel et al, Studies on the Transformation of Intact Yeast Cells by the LiAc/SS-DNA/PEG Procedure, Yeast, 1995, p. 355-360, vol. 11.
Supplementary European Search Report, European Patent Application No. 09719237.1, dated Jun. 1, 2011.
Benatuil, Lorenzo, et al. "An improved yeast transformation method for the generation of very large human antibody libraries." Protein Engineering, Design & Selection, 23:155-159 (2010).
Swers, et al.; Shuffled antibody libraries created by in vivo homologous recombination and yeast surface display; Nucleic Acids Research; 2004; vol. 32, No. 3; 8 pages.
Wu, et al.; High efficiency transformation by electroporation of Pichia pastoris pretreated with lithium acetate and dithiothreitol; BioTechniques, 2004, vol. 36, No. 1; pp. 152-154.

* cited by examiner

METHODS FOR TRANSFORMING YEAST

RELATED APPLICATION

This application claims priority to and the benefit of U.S. Provisional Application No. 61/067,910, filed Mar. 3, 2008.

FIELD OF THE INVENTION

The invention relates to the fields of yeast transformation and yeast cells and yeast cell libraries transformed thereby, and the production of recombinant products therefrom. More specifically, the present invention relates to the transformation of yeast by electroporation.

BACKGROUND OF THE INVENTION

Therapeutic antibodies generated using animal immunizations in vivo or by recombinant antibody display technology in vitro have been successful in the clinic and as such have validated these technologies as effective drug discovery techniques. While it is typically expected that monoclonal antibodies derived from animal immunizations are of sufficiently high affinity to achieve therapeutic efficacy, developing therapeutic antibodies from animal immunizations requires either humanization of the non-human antibodies or access to transgenic animals expressing human antibodies. Direct selection of fully human antibodies from pre-established antibody libraries by in vitro display technologies (phage, bacterial, yeast, mammalian cell, and ribosomal displays) (Chao, G. et al. (2006) *Nat. Protoc.* 1:755-68; Gai, S. A. and Wittrup, K. D. (2007) *Curr. Opin. Struct. Biol.* 17:467-73; Griffiths, A. D. et al. (1994) *EMBO J.* 13:3245-60; He, M. and Khan, F. (2005) *Expert Rev. Proteomics* 2:421-30; Hoogenboom, H. R. (2002) *Methods Mol. Biol.* 178:1-37; Hoogenboom, H. R. (2005) *Nat. Biotechnol.* 23:1105-16) offers a valuable parallel approach and may present the best alternative in cases where the target antigen fails to elicit a productive immune response in vivo.

Human antibody libraries have been engineered to display full-length antibody or various antibody fragments such as Fab, scFv, and dAb. The libraries are generally constructed by either capturing and transferring antibody diversities from B cell repertoires into the library with or without additional introduction of synthetic diversity (Hoet, R. M. et al. (2005) *Nat. Biotechnol.* 23:344-8), or by synthetically randomizing CDR residues in limited human antibody frameworks (Rothe, C. et al. (2008) *J. Mol. Biol.* 376:1182-200). Because the antibody heavy and light chains are separately amplified and reformatted into the library display format, new pairings between VH and VL are formed during this process. While this VH-VL shuffling allows the creation of novel antigen binding sites, it also very significantly increases the theoretical library diversity. Several strategies have been developed to engineer better and more productive antibody libraries by reducing the theoretical library diversity and the actual library size required to effectively sample the library. These strategies include intelligently designing synthetic or semi-synthetic libraries (Rothe, C. et al. (2008) *J. Mol. Biol.* 376:1182-200) and immune (Hoet, R. M. et al. (2005) *Nat. Biotechnol.* 23:344-8) or pseudoimmune (Lee, H. W. et al. (2006) *Biochem. Biophys. Res. Commun.* 346:896-903) libraries generated from less diverse but potentially more reactive B cell repertoires. Although these approaches may be effective in significantly reducing the theoretical library diversity by several or even many logs, the need for large library sizes and methods to generate them will always complement library designs in order to increase the chances of identifying antibody hits regardless of their scarcity.

The availability of means for the production of nucleic acid libraries and recombinant products produced thereby, such as pharmaceutical proteins, in eukaryotic systems such as yeast, provides significant advantages relative to the use of prokaryotic systems such as *E. coli*. Yeast can generally be grown to higher cell densities than bacteria and are readily adaptable to continuous fermentation processing. However, the development of yeast species as host/vector systems for the production of recombinant products and libraries is severely hampered by the lack of knowledge about transformation conditions and suitable means for stably introducing foreign nucleic acids into the yeast host cell.

Among the various electrical and biological parameters that facilitate electrotransformation of cells is the adsorption of DNA to the cell surface. Alternating electric fields of low intensity also promote DNA transfer into *E. coli* bacteria, presumably by the electrical stimulation of DNA permeases. Evidence for the dominant electrodiffusive or electrophoretic effect on electroporative gene transfer of polyelectrolyte DNA has accumulated. Electroosmotic effects and membrane invagination facilitated by electroporation have also been reported.

The application of an electrical field across a yeast cell membrane results in the creation of transient pores that are critical to the electroporation process. An electroporator signal generator provides the voltage (in kV) that travels across the gap (in cm) between the electrodes. This potential difference defines what is called the electric field strength where E equals kV/cm. Each cell has its own critical field strength for optimum electroporation. This is due to cell size, membrane make-up and individual characteristics of the cell wall itself. For example, mammalian cells typically require between 0.5 and 5.0 kV/cm before cell death and/or electroporation occurs. Generally, the required field strength varies inversely with the size of the cell.

Methods of Transformation

1. Transformation by Electroporation

Becker et al. (Methods in Enzymology 194: 182-187 (1991)) disclose methods of transformation of the yeast *Saccharomyces cerevisiae* (*S. cerevisiae*). Becker also discloses spheroplast transformation.

Faber et al. (Curr. Genet. 25: 305-310 (1994)) disclose methods for transformation of the methylotropic yeast *Hansenula polymorpha*. Faber also applied the method to *Pichia methanolica*.

Helmuth et al. (Analytical Biochem. 293:149-152 (2001)) disclose increased yeast transformation efficiency by combining both LiAc and DTT pretreatments.

Kasutske et al. (Yeast 8: 691-697 (1992)) disclose electropulse transformation of intact *Candida maltosa* cells by different homologous vector plasmids.

Meilhoc et al. (Bio/Technology 8: 223-227 (1990)) disclose a transformation system using intact *S. cerevisiae* yeast cells and electric field pulses.

Neumann et al. (1996) Biophys. J. (1996) 71:868-877 disclose kinetics of yeast cell transformation by electroporation and calcium-mediated DNA adsorption.

Piredda et al. (Yeast 10: 1601-1612 (1994)) disclose a transformation system for the yeast Yamadazyma (*Pichia*) ohmeri.

Scorer et al. (Bio/Technology 12: 181-184 (1994)) disclose *P. pastoris* vectors allowing for rapid G418 selection of rare high copy number transformants for expression in *Pichia pastoris* using both electroporation and spheroplast transformation systems.

Sherman et al. (Laboratory Course Manual for Methods in Yeast Genetics, pages 91 102, Cold Spring Harbor Laboratory (1986)) disclose transformation of yeast mutants LEU2 and HIS3.

Suga and Hatakeyama (Curr. Genet. 43:206-211 (2003)) disclose a freezing method to generate competent cells prior to electroporation with addition of calcium.

Thompson et al. (Yeast 14:565-571 (1998)) disclose the preparation of yeast cells such as *S. cerevisiae* and *Candida albicans* for transformation by electroporation.

Yang et al. (Applied and Environmental Microbiology 60(12): 4245-4254 (1994)) disclose electroporation of *Pichia stipitis* based on its URA3 gene and a homologous autonomous replication sequence ARS2.

U.S. Pat. No. 5,716,808 to Raymond discloses methods for preparing *Pichia methanolica* cells containing foreign DNA constructs using electroporation and methods for producing foreign peptides in *Pichia methanolica* cells.

U.S. Pat. No. 7,009,045 to Abbas discloses the transformation of the flavinogenic yeasts, *Pichia guilliermondii* and *Candida famata*, by electroporaiion and by spheroplast transformation.

2. Transformation by Spheroplast Formation

Becker et al. (Methods in Enzymology 194: 182-187 (1991)) disclose methods of transformation of the yeast *S. cerevisiae* as well as spheroplast transformation.

Scorer et al. (Bio/Technology 12: 181-184 (1994)) disclose *P. pastoris* vectors allowing for G418 selection of rare high copy number transformants for expression in *Pichia pastoris* using both electroporation and spheroplast transformation systems.

U.S. Pat. No. 4,808,537 to Stroman et al. discloses a method for isolating and cloning a methanol inducible gene from *Pichia pastoris* and the regulatory regions useful for the methanol regulation expression of heterologous genes using spheroplast transformation.

U.S. Pat. No. 4,837,148 to Cregg et al. disclose autonomous replication sequences that are capable of maintaining plasmids as extra-chromosomal elements in host strains of *Pichia*. The patent further discloses constructs including the DNA sequences as well as transformed organisms produced by spheroplast formation and provides processes for producing the DNA sequences and constructs of the invention, as well as methods for isolating the sequences from any source.

U.S. Pat. No. 4,855,231 to Stroman et al. discloses DNA sequences that are responsive to the presence of methanol, catabolite non-repressing carbon sources and carbon source starvation. The '231 patent demonstrates spheroplast transformation of *Pichia pastoris*.

U.S. Pat. No. 4,879,231 to Stroman et al. discloses a spheroplast transformation method for the yeast such as *Pichia pastoris*.

U.S. Pat. No. 4,882,279 to Cregg et al. discloses a spheroplast transformation technique for yeasts of the genus *Pichia*, for example, *Pichia pastoris*.

U.S. Pat. No. 5,135,868 to Cregg relates to a method for the site specific genomic modification of yeasts of the genus *Pichia*. The '868 patent uses a spheroplast transformation method.

U.S. Pat. No. 5,268,273 to Buckholz relates to a method of spheroplast transformation of *Pichia pastoris*.

U.S. Pat. No. 5,736,383 to Raymond relates to a method of transformation of yeast strains of the genus *Pichia*, particularly *Pichia methanolica*. The '383 patent further relates to a method of spheroplast transformation of yeasts of the genus *Pichia* as well as a method of transformation by electroporation.

3. Other Transformation Systems

Kunze et al. (Current Genetics 9(3): 205-209 (1985)) disclose a method of transformation of *S. cerevisiae*, *Candida maltosa* and *Pichia guilliermondii* G266 with the plasmid pYe (ARG4)-411, which contains the *S. cerevisiae* ARG4 gene inserted into pBR322. Kunze used $CaCl_2$ in the method of transformation.

Kunze et al. (J. Basic Microbiol. 25(2): 141-144 (1985)) disclose a method of transformation of the industrially important yeasts *Candida maltosa* and *Pichia* guilliermondii G266 using $CaCl_2$.

Kunze et al. (Acta Biotechnol. 6(1): 28 (1986)) disclose transformations of the industrially important yeasts *Candida maltosa* and *Pichia* guilliermondii.

Neistat et al. (Mol. Ge. Mikrobiol. Virusol. 12: 19-23 (1986)) (Abstract only) disclose transformation of *Hansenula polymorpha, Pichia guilliermondii, Williopsis saturnus* yeast by a plasmid carrying the ADE2 gene of *S. cerevisiae*. The method of transformation is not disclosed.

U.S. Pat. No. 4,929,555 to Cregg et al. discloses a method for making whole cells of methylotrophic species of genus *Pichia* competent for transformation by DNA and a method for transforming with DNA whole cells of such species, particularly *Pichia pastoris*.

U.S. Pat. No. 5,231,007 to Heefner et al. disclose a method of generating and isolating highly flavinogenic strains of *Candida famata* which produce riboflavin yields of around 7.0 to 7.5 grams per liter per 6 days. The method includes a combination of iterative mutagenizing steps and protoplast fusion steps performed on the parent strain and the descendent strains that are selected following each step according to a screening protocol.

4. Vectors, ARS Elements and Gene Libraries

Clyne, R. K. et al. (EMBO J. 14(24): 6348-6357 (1995)) relates to a fine structure analysis of ARS1, an ARS element of the fission yeast *Schizosaccharomyces pombe*. Characterization of a series of nested deletion mutations indicated that the minimal fragment of DNA encompassing ARS1 is large since no fragment under 650 bp retained significant ARS activity.

Liauta-Teglivets, O. et al. (Yeast 11(10): 945-952 (1995)) disclose the cloning of the structural gene of GTP-cyclohydrolase involved in riboflavin biosynthesis from a *Pichia guilliermondii* genomic library.

Cannon, R. D. et al. (Mol. Gen. Genet. 221(2): 210-218 (1990)) disclose isolation and nucleotide sequence of an autonomously replicating sequence (ARS) element functional in *Candida albicans* and *S. cerevisiae*.

Takagi, M. et al. (J. Bacteriol. 167(2): 551-555 (1986)) disclose construction of a host-vector system in *Candida maltosa* by using an ARS site isolated from its genome.

Pla, J. et al. (Gene 165(1): 115-120 (1995)) relates to ARS2 and ARS3 *Candida albicans* DNA fragments with autonomous replicating activity shown to promote non-integrative genetic transformation of both *Candida albicans* and *S. cerevisiae*.

U.S. Pat. No. 5,212,087 to Fournier et al. discloses ARS sequences that are efficacious in *Yarrowia lipolytica* as well as plasmids carrying these sequences.

U.S. Pat. No. 5,665,600 to Hagenson et al. discloses *Pichia pastoris* linear plasmids and DNA fragments thereof which contain ARS sequences. The '600 patent used the spheroplast transformation system as described in Cregg et al in U.S. Pat. No. 4,929,555.

U.S. Pat. No. 4,837,148 to Cregg et al. discloses autonomous replication sequences that are capable of maintaining plasmids as extrachromosomal elements in host strains of *Pichia*. The '148 patent further relates to constructs including the DNA sequences as well as transformed organisms therewith. The patent additionally provides processes for producing the DNA sequences and constructs of the invention, as well as methods for isolating the sequences from any source.

Chao et al. (Nature Protocols, 1 (2):755-768 (2006)) discloses a protocol for transforming yeast cells by electroporation and achieving a maximal $5 \times 10^7$ library size with 5 µg insert and 1 µg vector DNA.

The above methods and disclosures while achieving increasingly higher transformation efficiency are still laborious and take significant time and repetitive efforts to accumulate multiple small libraries in the $10^6$ to $10^7$ size ranges to a larger and combined library size in the $10^8$ to $10^9$ size range.

Yeast libraries have not achieved the size or efficiency that has been achieved by phage libraries. As reviewed by Hoogenboom in 2005 (Nature Biotech., 23(9):1105-1116), a typical maximal phage library size for is $10^{10}$ to $10^{11}$, whereas a typical yeast library is $10^7$ in size (significantly smaller than those achieved by other display technologies (Hoogenboom, H. R. (2002) *Methods Mol. Biol.* 178:1-37; Hoogenboom, H. R. (2005) *Nat. Biotechnol.* 23:1105-16), although library sizes in the $10^9$ range have been previously reported (Hoet, R. M. et al. (2005) *Nat. Biotechnol.* 23:344-8; Lipovsek, D. et al. (2007) *J. Mol. Biol.* 368:1024-41; Segal, L. et al. (2007) *Bioinformatics* 23:1440-9. Feldhaus et al. (Nature Biotech., 21:163-170 (2003)) has shown that a $1.5 \times 10^9$ library can be constructed by laboriously repeating the transformation and then combining transformed libraries. Although recent progress in electroporation protocols (see Chao, Nature Protocols 1(2):755-768 (2006)) has made it possible to achieve a maximal $5 \times 10^7$ yeast library size in a single transformation, we have found that the Chao protocol typically transforms yeast at a significantly lower transformation efficiency. It is still a correct statement that yeast library sizes achieved to date are still significantly below what is routinely achievable by phage display libraries in the $10^{10}$ to $10^{11}$ size.

Yeast display library selection, using both magnetic bead and fluorescence-activated cell sorting, offers an efficient and sensitive method to enrich specific binders to target antigens, in particular by its compatibility with fluorescence activated cell sorting (FACS). The advantage of this selection power, however, is hampered by the limited size of typical yeast display libraries due to the low transformation efficiency of yeast cells. If the yeast display selection technology could be coupled with large antibody libraries similar to those made for phage display (about $10^{10}$ in size), yeast display technology would provide an extremely effective antibody discovery tool.

A need therefore exists for efficient methods for producing protein libraries, e.g., antibody libraries, using yeast.

SUMMARY OF THE INVENTION

The invention provides highly efficient and rapid methods of transforming yeast cells, for example for the production of yeast cell libraries up to $2 \times 10^{10}$ in size. The methods of the invention make it possible to achieve yields on the scale of phage libraries. The methods of the invention remove a significant bottleneck in applying yeast display technology as a practical tool to access a much larger antibody diversity space previously unexplored, and the library size is now only limited by the size of yeast culture that can be grown in laboratories.

Multiple components and conditions including the use of $CaCl_2$, $MgCl_2$, sucrose, sorbitol, lithium acetate, dithiothreitol, electroporation voltage, DNA input, and cell volume were tested or titrated to identify the best combination. By applying this newly developed protocol a $2 \times 10^{10}$ antibody library was constructed from human spleen RNA essentially in one day with a typical transformation efficiency of $1-1.5 \times 10^8$ transformants per microgram of vector DNA. Sequence analysis confirmed diverse representation of antibody germline sequences within this non-immune human spleen antibody library. By performing pilot library selections we have identified human antibodies to TNF-α and IL-18 with low nanomolar affinities, demonstrating productivity of this library.

In one aspect, the invention provides methods of preparing a yeast library by electroporation of the yeast cells, the method comprising the steps of (a) providing a suspension comprising nucleic acid vectors, yeast cells, sorbitol, and $CaCl_2$; and (b) electroporating the suspension at 0.5 kV/cm to greater than 12.5 kV/cm with a capacitance of about 10 to about 50 µF. In an embodiment, the invention provides methods for transforming yeast with DNA to prepare a library, the method comprising the steps of (a) culturing yeast cells to an $OD_{600}$ of about 1.0 to about 2; (b) washing the yeast cells in a volume of cold water; (c) washing the yeast cells in a volume of cold 1M sorbitol/1 mM $CaCl_2$; (d) incubating the yeast cells in a volume of 30° C. 0.1M LiAc/10 mM DTT; (e) washing the yeast cells in a second volume of cold 1M sorbitol/1 mM $CaCl_2$; (f) resuspending the yeast cells in a third volume of cold 1M sorbitol/1 mM $CaCl_2$ to form a yeast cell electroporation suspension; (g) adding a volume of the electroporation cell suspension to vector DNA and insert DNA to form a yeast cell—DNA electroporation suspension; and (h) electroporating the yeast cell—DNA electroporation suspension at a voltage of between about 2.5 kV/cm and about 12.5 kV/cm in a 0.2 cm gap cuvette.

The ratio of vector DNA to insert DNA is in the range of about 1:0.5 to about 1:10, for example, 1:0.5; 1:1; 1:2; 1:3; 1:4; 1:5; 1:6; 1:7; 1:8; 1:9, or 1:10. In an embodiment, about 1 µg of vector DNA and about 1 µg of insert DNA are used in a reaction. In another embodiment, about 1 µg of vector DNA and about 2 µg of insert DNA are precipitated. In another embodiment, about 1 1 g of vector DNA and about 3 g of insert DNA are precipitated. In still another embodiment, about 1 µg of vector DNA and about 4 µg of insert DNA are precipitated. In yet another embodiment, about 1 µg of vector DNA and about 5 µg of insert DNA are precipitated.

In an embodiment, the cell suspension comprises about 50 to about 400 µl of yeast cells, for example, about 50, 100, 150, 200, 250, 300, 350, 400 µl of yeast cells.

In an embodiment, the yeast cells suspension is about 1 to about $10 \times 10^9$ yeast cells/mL, for example, about 1, about 2, about 3, about 4, about 5, about 6, about 7, about 8, about 9, or about $10 \times 10^9$ yeast cells/mL.

In an embodiment, the field strength used to electroporate the yeast cells was about 0.5 kV/cm to about 12.5 kV/cm, for example, about 0.5, about 1.0, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10.0, about 10.5, about 11.0, about 11.5, about 12.0, about 12.5, about 13.0, about 13.5, about 14.0, about 14.5, or about 15.0 kV/cm, In an embodiment, the yeast cells are electroporated at a capacitance of about 10 to about 50 μF, for example, about 10, about 15, about 20, about 25, about 30, about 35, about 40, about 45, or about 50, In an embodiment, the yeast cells are suspending in about 0.1 to about 10M sorbitol and about 0.1 to about 10 mM $CaCl_2$ or $MgCl_2$, for example, about 0.1, about 0.25, about 0.5, about 0.75, about 1.0, about 2.0, about 3.0, about 4.0, about 5.0, about 6.0, about 7.0, about 8.0, about 9.0, or about 10.0 M sorbitol, or, for example, about 0.1, about 0.25, about 0.5, about 0.75, about 1.0, about 2.0, about 3.0, about 4.0, about 5.0, about 6.0, about 7.0, about 8.0, about 9.0, or about 10.0 mM $CaCl_2$ or $MgCl_2$, In an embodiment, the yeast cells are incubated in about 0.01 to about 1.0 M LiAc, for example, about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, or about 1.0 M LiAc, and/or about 1 to about 100 mM DTT, for example, about 1, about 10, about 20, about 30, about 40, about 50, about 60, about 70, about 80, about 90, or about 100 mM DTT.

In a particular embodiment, the invention provides methods for transforming yeast with DNA to prepare a library, the method comprising two or more of the steps of (a) culturing yeast cells overnight to an $OD_{600}$ of about 1.0 to about 2.0; (b) washing the yeast cells in water; (c) washing the yeast cells in a solution comprising sorbitol and $CaCl_2$; (d) incubating the yeast cells in a solution comprising LiAc and DTT; (e) washing the yeast cells in a solution comprising sorbitol and $CaCl_2$; (f) resuspending the yeast cells in a volume of a solution comprising sorbitol and $CaCl_2$ to form a yeast cell electroporation suspension; (g) adding a volume of the electroporation cell suspension to vector DNA and insert DNA to form a yeast cell—DNA electroporation suspension; and (h) electroporating the yeast cell—DNA electroporation suspension at a voltage of between about 2.5 kV/cm and about 12.5 kV/cm in a 0.2 cm gap cuvette.

In another particular embodiment, the invention provides methods for transforming yeast with DNA, the method comprising two or more steps of: (a) minimizing the volume of vector and insert DNA in a ratio of from about 1:0.5 to about 1:10 by precipitating DNA into a pellet followed by resuspending in a minimal volume; (b) culturing yeast cells from a colony to an appropriate growth state by (i) inoculating a first volume of medium with a yeast colony from a growth plate or a portion of a growing yeast culture; (ii) growing the yeast cells overnight at 30° C.; (iii) inoculating a second volume of medium with the cells from step (ii) and growing the cells at 30° C. until they reach an $OD_{600}$ of about 1.3 to about 1.6; (c) pelleting the yeast cells by centrifugation; (d) washing the yeast cells with cold water; (e) washing the yeast cells with cold 1M sorbitol/1 mM $CaCl_2$; (f) resuspending the yeast cells in 0.1M LiAc/10 mM DTT; (g) incubating the yeast cells at 30° C. at 250 rpm for 30 minutes; (h) washing the yeast cells with 1M sorbitol/1 mM $CaCl_2$; (i) resuspending the yeast cells in 1M sorbitol/1 mM $CaCl_2$ to form a yeast cell electroporation suspension; (j) adding a portion of the yeast cell electroporation suspension to the DNA pellet to form a yeast cell—DNA electroporation suspension; (k) electroporating the yeast cell—DNA electroporation suspension in a range of about 0.5 kV to about 2.5 kV and a 25 uF capacitance; (l) adding a 1:1 mix of 1M sorbitol/YPD (final concentration: 0.5M sorbitol, 0.5×YPD) to the electroporated yeast cell-DNA electroporation suspension and incubating at 30° C. for 1 hour; and (m) pelleting the yeast cells and resuspending in 10 ml 1M sorbitol.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which.

DETAILED DESCRIPTION OF THE INVENTION

A highly efficient electroporation protocol for *Saccharomyces cerevisiae* was established by testing and combining several previously identified conditions (Chao, G. et al. (2006) *Nat. Protoc.* 1:755-68; Becker, D. M. and Guarente, L. (1991) *Methods Enzymol.* 194:182-7; Helmuth, M. et al. (2001) *Anal. Biochem.* 293:149-52; Neumann, E. et al. (1996) *Biophys. J.* 71:868-77; Simon, J. R. (1993) *Methods Enzymol.* 217:478-83; Suga, M. and Hatakeyama, T. (2003) *Curr. Genet.* 43:206-11; Thompson, J. R. et al. (1998) *Yeast* 14:565-71. These include the combination of lithium acetate (LiAc) and dithiothreitol (DTT) as cell conditioning agents, both of which have been used to enhance the frequency of yeast transformation (Helmuth, M. et al. (2001) *Anal. Biochem.* 293:149-52; Thompson, J. R. et al. (1998) *Yeast* 14:565-71; Gietz, R. D. et al. (1995) *Yeast* 11:355-60), and the inclusion of sorbitol and calcium chloride (Becker, D. M. and Guarente, L. (1991) *Methods Enzymol.* 194:182-7; Helmuth, M. et al. (2001) *Anal. Biochem.* 293:149-52; Neumann, E. et al. (1996) *Biophys. J.* 71:868-77) in the electroporation buffer.

DEFINITIONS

The term "expression vector" means a DNA construct that includes an autonomous site of replication (ARS), a site of transcription initiation and at least one structural gene coding for a protein that is to be expressed in the host organism. A site of replication, or origin of replication, is any DNA sequence that controls the replication of the cloning and expression vectors. An expression vector usually also contains appropriate control regions such as one or more enhancers and/or promoters, suppressors and/or silencers, and terminators that control the expression of the protein in the host yeast. Expression vectors according to the present invention may also contain a selection marker comprising an essential gene as described herein. The expression vector also optionally contains other selectable markers widely available and well known to those of skill in the art. Expression vectors are one type of vector. Vectors may optionally include one or more ARS sequences (elements) from one or more strains of yeast.

The term "operably linked" means that DNA segments are arranged so that they function in concert for their intended purposes, e.g., transcription initiates in the promoter and proceeds through the coding segment to the terminator.

The term "transformation" means the introduction of DNA or other nucleic acids into a recipient yeast host cell that changes the genotype.

The term "transformant," or a "transformed cell," means a recipient yeast host cell, and progeny thereof, that has undergone transformation.

Vectors useful in the electroporation methods of the invention include the pYD vector any other vectors and their derivative constructs that can be propagated by yeast cells, or nucleic acids in general. The expression vector of the present invention may be based on any type of vector as long as the vector can transform, transfect or transduce a host yeast cell. In a preferred embodiment, the expression vector is based on a yeast plasmid, especially one from *S. cerevisiae*. After transformation of yeast cells, the exogenous DNA encoding the library sequences is taken up by the cells and subsequently expressed by the transformed cells.

More preferably, the expression vector may be a yeast-bacteria shuttle vector that can be propagated in either *E. coli* or yeast (Struhl, et al. (1979) Proc. Natl. Acad. Sci. 76:1035-1039). The inclusion of *E. coli* plasmid DNA sequences, such as pBR322, facilitates the quantitative preparation of vector DNA in *E. coli*, and thus the efficient transformation of yeast.

The types of yeast plasmid vectors that may serve as the shuttle may be a replicating vector or an integrating vector. A replicating vector is a yeast vector that is capable of mediating its own maintenance, independent of the chromosomal DNA of yeast, by virtue of the presence of a functional origin of DNA replication. An integrating vector relies upon recombination with the chromosomal DNA to facilitate replication and thus the continued maintenance of the recombinant DNA in the host cell. A replicating vector may be a 2 micron-based plasmid vector in which the origin of DNA replication is derived from the endogenous 2 micron plasmid yeast. Alternatively, the replicating vector may be an autonomously replicating (ARS) vector, in which the "apparent" origin of replication is derived from the chromosomal DNA of yeast. Optionally, the replicating vector may be a centromeric (CEN) plasmid that carries in addition to one of the above origins of DNA replication a sequence of yeast chromosomal DNA known to harbor a centromere.

The vectors may be transformed into yeast cells in closed circular form or in a linear form. Transformation of yeast by integrating vectors, although with heritable stability, may not be efficient when the vector is in a close circular form (e.g., yielding only about 1-10 transformants per μg of DNA). Linearized vectors, with free ends located in DNA sequences homologous with yeast chromosomal DNA, transform yeast with higher efficiency (100-1000 fold) and the transforming DNA is generally found integrated into sequences homologous to the site of cleavage. Thus, by cleaving the vector DNA with a suitable restriction endonuclease, it is possible to increase the efficiency of transformation and target the site of chromosomal integration. Integrative transformation may be applicable to the genetic modification of brewing yeast, providing that the efficiency of transformation is sufficiently high and the target DNA sequence for integration is within a region that does not disrupt genes essential to the metabolism of the host cell.

ARS plasmids, which have a high copy number (approximately 20-50 copies per cell), tend to be the most unstable, and are lost at a frequency greater than 10% per generation. However, the stability of ARS plasmids can be enhanced by the attachment of a centromere; centromeric plasmids are present at 1 or 2 copies per cell and are lost at only approximately 1% per generation. Non-limiting examples of proteins for expression by yeast host cells using the electroporation methods of the invention include any genes of interest include antibodies and antibody fragments, hormones, cytokines and lymphokines, receptors, adhesion molecules, and enzymes.

Yeast strains that can be transformed by the electroporation method of the invention include yeast species in the *Saccharomyces* genus such as *Saccharomyces cerevisiae* and the *Schizosaccharomyces* genus such as *Schizosaccharomyces Pombe*. In one embodiment, the yeast cells are diploid yeast cells. Alternatively, the yeast cells are haploid cells such as the "a" and "α" strain of yeast haploid cells.

The invention provides methods for the transformation of yeast cells comprising electroporating a cell suspension containing yeast together with one or more nucleic acid constructs. The transformation of yeast cells can result in anywhere from a single clone to population of yeast cells (i.e., yeast library or libraries) that can be used to screen for (a) peptide(s) or protein(s) displayed on the surface of yeast cells by means of tethering to a yeast surface protein or association via a specific covalent bond or non-covalent interaction with yeast cell surface proteins or other components; (b) peptide(s) or protein(s) expressed intracellularly; or (c) peptide(s) or protein(s) that are secreted into extracellular space such as culture media, or deposited onto solid surface. Such yeast libraries can be conveniently amenable to multiple applications, to screen or characterize interactions between the peptide(s) or protein(s) to another protein, peptide, DNA, RNA or other chemical matters that can be introduced into the yeast cells or exogenously added. Specific examples are those found in yeast display, yeast two hybrid, yeast three hybrid, etc.

The invention provides a method for the transformation of yeast cells comprising electroporating a cell suspension containing yeast together with one or more nucleic acid constructs comprising one or more regulatory sequences and one or more genes or gene segments, using one or more of resistance, field strength and pulse duration sufficient to transform the yeast cells.

In an embodiment, field strength is from about 2.5 kV/cm to about 12.5 kV/cm. In certain embodiments, the field strength is about 0.5 kV/cm, about 1.0 kV/cm, about 1.5 kV/cm, about 2.0 kV/cm, or about 2.5 kV/cm. These values take into account that the electroporation cuvette has a 0.2 cm gap. Higher field strengths are possible but their practicality is largely dependent upon the development of an apparatus that can deliver a stronger pulse.

In an embodiment, the pulse duration is from about 3 milliseconds to about 10 milliseconds. In a particular embodiment, the pulse duration is about 4.8 milliseconds.

Treatment of cells by the electroporation methods of the invention is carried out by applying an electric field to a yeast cell suspension between a pair of electrodes. The field strength must be adjusted reasonably accurately so that electroporation of the cells occurs without damage, or at with minimal damage, to the cells. The distance between the electrodes can then be measured and a suitable voltage according to the formula $E=V/d$ can then be applied to the electrodes (E=electric field strength in V/cm; V=voltage in volts; and d=distance in cm).

Pulse generators for carrying out the procedures described herein are and have been available on the market for a number of years. One suitable signal generator is the Gene Pulser II (Bio-Rad Laboratories, Inc., Hercules, Calif.). A typical set up consists of the Gene Pulser II connected to a capacitance expender plus and the pulse controller plus modules.

Additional electroporation models available commercially include the Gene Pulser Mxcell system or the Gene Pulser X cell eukaryotic system (Bio-Rad), the CelljecT Pro Electroporator (Thermo Scientific), Multiporator Electroporation Systems and other Eppendorf® Electroporation Systems (Eppendorf, North America), ECM electroporation generators and BTX® HT 96 Well Electroporation System (BTX, Harvard apparatus), all of which are suitable apparatus for electroporating yeast cells using the conditions disclosed herein.

Electroporation is used within the present invention to facilitate the introduction of DNA into yeast cells. Electroporation is the process of using a pulsed electric field to transiently permeabilize cell membranes, allowing macromolecules, such as DNA, to pass into cells. However, the actual mechanism by which DNA is transferred into the cells is not well understood. For transformation of *Candida famata*, for example, electroporation is surprisingly efficient when the cells are exposed to an experimentally decaying pulsed electric field having a field strength of from about 10 to about 13 kV/cm and a resistance value of about R5 (129 ohms), and a time constant of about 4 5 ms. Typically, resistance and capacitance are either present or may be selected by the user, depending on the electroporation equipment selected. In any event, the equipment is configured in accordance with the manufacturer's instructions to provide field strength and decay parameters as appropriate.

The invention further relates to highly efficient methods of transformation of yeasts that allow for a high level of expression of any one or more desired endogenous (i.e., naturally existing within that yeast cell) or heterologous genes. The methods of the invention further relate to a method for preparing libraries, for example, that express antibodies or chimeras or fragments thereof.

In one scenario, expression vectors carrying genes of interest can be transformed into yeast host cells by electroporation to generate a single clone or a library comprised of many transformed cells expressing intracellular proteins (e.g., nuclear or cytoplasmic proteins), membrane proteins (e.g., membrane-spanning proteins or membrane attached proteins), or secreted proteins. One will be able to use the transformed cells or library to purify proteins, study protein functions, identify protein-protein interactions, or to identify novel protein binders or interaction partners. Of important note is the ability to generate very large yeast libraries displaying or expressing antibodies and antibody fragments. The library can be subjected to selection by target antigens to identify antibodies that bind to the selecting antigens.

As transformed yeast have a tendency to lose artificially-constructed plasmids, it is advantageous to use a culture medium so as to exert a positive selection pressure on them. When the strain is an auxotrophic mutant for an essential metabolite and when the vector plasmid used comprises a marker gene capable of restoring the strain prototrophy, for example, the LEU2 gene mentioned above, this selection pressure may be exerted by omitting the metabolite from the culture medium. Other means exist to obtain the same result and may also be used to practice the invention.

Depending upon the nature of the structural gene of interest, the product or expression product may remain in the cytoplasm of the yeast host cell or be secreted. It has been found that not only the proteins that remain in the cell but also those that are secreted are soluble. Where the product or expression product is to remain in the yeast host cell, it may generally be desirable to have an inducible transcription initiation region, so that until the transformant has reached a high density, there is little or no expression or production of the desired product. After sufficient time for the product or expression product to be expressed, the cells may be isolated by conventional means, e.g., centrifugation, lysis and the product of interest isolated. Depending upon the nature and use of the product, the lysate may be subjected to various purification methods, such as chromatography, electrophoresis, solvent extraction, crystallization, dialysis, ultrafiltration or the like. Methods of chromatography include, but are not limited to, gas chromatography, HPLC, column chromatography, ion exchange chromatography and other methods of chromatography known to those of skill in the art. The degree of purity may vary from about 50%, to 90% or higher, preferably up to about 100%.

Alternatively, the expression product or product of interest may be secreted into the culture medium, and produced on a continuous basis, where the medium is partially withdrawn, the desired product extracted, e.g., by column or affinity chromatography, ultrafiltration, precipitation or the like, and the spent medium discarded or recirculated by restoring essential components. The permeate containing the product from the ultrafiltration can be further subjected to concentration, further by evaporation, followed by crystallization or precipitation using alcohol and/or pH adjustment. Those of skill in the art are aware of the many process options. When the product is to be secreted, normally a constitutive transcriptional initiation region will be employed, although non-constitutive regions may be used.

Unless otherwise indicated, all nucleotide sequences newly described herein were determined using an automated DNA sequencer (such as, for example, the Model 377 from PE Applied Biosystems, Inc.). Therefore, as is known in the art, for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art.

EXEMPLIFICATION

Example 1

Preparation of Vector DNA pYDsTev vector was digested with the restriction enzymes SfiI and NotI for use in recombination with the scFv+300 bp DNA fragments. To improve efficiency and prevent uncut vector from being transformed, the SfiI/NotI digested vector was further digested with BglII and HpaI (both cut within stuffer).

The digested DNA was purified using Sureclean from Bioline (Randolph, Mass.). In brief, the restriction digestion was mixed with an equal volume of Sureclean. Samples were incubated for 10 minutes at room temperature. Samples were then centrifuged for 15 minutes at 13.2 k rpm. Supernatant was discarded and pellets were washed with 2.5× sample volume of 70% ethanol. Samples were then centrifuged for 15 minutes at 13.2 k rpm. Supernatant was removed and pellets were air dried. Pellets were resuspended in 5-10 µL TE pH 8.

Example 2

Preparation of Insert DNA

Insert DNA is prepared using PCR to amplify an insert of interest adding sufficient vector sequence 5' and 3' (e.g., about 300 base pairs) to the insert to efficiently perform homologous recombination.

Immunoglobin constant region primers were designed (Table 2) that hybridize to IgM and IgG (for IgM/G cDNA) or IgK (IgK cDNA) of immunoglobins for 1st Strand cDNA synthesis. Specifically, for IgM/G cDNA primers FcgRev1, 2, and 3 and FcmRev1, 2 and 3 were utilized. For the IgK 1st Strand cDNA synthesis Ckrev1, 2, and 3 were utilized.

cDNA synthesis reactions were performed using the Invitrogen 1st Strand Synthesis kit using the above primers.

TABLE 1

Exemplary PCR Reactions (Step 1)

| IgM/G cDNA | IgK cDNA |
|---|---|
| 20 µl of 50 ng/µl CloneTech polyA spleen RNA | 10 µl of 50 ng/µl CloneTech polyA spleen RNA |
| 3 µl of 300 ng/µl FcgRev1 | 1.5 µl of 300 ng/µl CkRev1 |
| 3 µl of 300 ng/µl FcgRev2 | 1.5 µl of 300 ng/µl CkRev2 |
| 3 µl of 300 ng/µl FcgRev3 | 1.5 µl of 300 ng/µl CkRev3 |
| 3 µl of 300 ng/µl FcmRev1 | 10 µl dNTPs (10 mM) |
| 3 µl of 300 ng/µl FcmRev2 | 75.5 µl dd water |
| 3 µl of 300 ng/µl FcmRev3 | 100 µl total volume |
| 20 µl of dNTPs (10 mM) | |
| 142 µl dd water | |
| 200 µl total volume | |

50 µl/rxn, reactions at 65° C. for 5', then to 4° C. for 1 minute

TABLE 2

Oligonucleotides Utilized in This Study

| Oligo Name | Sequence | Description | SEQ ID NO. |
|---|---|---|---|
| Ckrev1 | TCCACCTTCCACTG | Ck Reverse primer 1 | SEQ ID NO: 1 |
| Ckrev2 | CAGGCACACAACAG | Ck Reverse primer 2 | SEQ ID NO: 2 |
| Ckrev3 | GAGTGTCACAGAGC | Ck Reverse primer 3 | SEQ ID NO: 3 |
| FcGrev1 | AGTTCCACGACACC | IgG reverse primer | SEQ ID NO: 4 |
| FcGrev2 | GAAGGTGTGCACG | IgG reverse primer | SEQ ID NO: 5 |
| FcGrev | CCACGCTGCTGAG | IgG reverse primer | SEQ ID NO: 6 |
| FcMrev1 | ACTTTGCACACCAC | IgM reverse primer | SEQ ID NO: 7 |
| FcMrev2 | TTTGTTGCCGTTGG | IgM reverse primer | SEQ ID NO: 8 |
| FcMrev3 | GGGAATTCTCACAGG | IgM reverse primer | SEQ ID NO: 9 |
| PYD5prev | GCGCCCTGAAAATACAGGTTTTC | Hybridizes at immediate upstream of the SfiI site in pYD vector. Used in conjunction with 5107 primer to generate about 300 bp extension added to scFv to enhance homolougous recombination efficiency | SEQ ID NO: 10 |

Step 2 of Synthesis:

45 µl of Master Mix (prepared stock comprising 80 µl RT Buffer (10×), 160 µl MgCl$_2$, 80 µl 0.1M DTT, 40 µl RNAse Out) was added to each chilled 50 µl reaction and the tubes placed at 42° C. for 2 minutes. 5 µl of SuperscriptII reverse transcriptase was added to each reaction tube and incubated at 42° C. for 50 minutes, transferred to 70° C. for 15 minutes, and then transferred to 4° C. 5 µl of RNAse H was added to each reaction and then incubated at 37° C. for 20 minutes. Four IgG/M reactions were pooled and two IgK reactions were pooled.

Example 3

Generation of Human Spleen IgG/M VH and IgK VL DNA

Human VH and VK immunoglobin diversity was amplified using oligonucleotide primers defined by Sblattero and Bradbury (1998) *Immunotechnology* 3:271-278.

| 8x 100 µl Sample VH reaction | |
|---|---|
| 80 µl | 10x PCR Reaction Buffer |
| 8 µl | dNTPs (10 mM) |
| 32 µl | MgSO$_4$ (50 mM) |
| 8 µl | VH back primer (20 µM) |
| 8 µl | equimolar mix of VH 1/2, VH4/5, VH3 and VH6 for (5 µM each/20 µM 3' primer total) |
| 16 µl | IgM/G cDNA |
| 8 µl | Platinum Taq HiFi |
| 640 µl | dd water |
| 100 µl/rxn | |
| 8x 100 µl Sample VK reaction | |
| 80 µl | 10x PCR Reaction Buffer |
| 8 µl | dNTPs (10 mM) |

-continued

| 32 µl | MgSO$_4$ (50 mM) |
|---|---|
| 8 µl | VK back primer (20 µM) |
| 8 µl | equimolar mix of VK1, VK2/4, VK3, and VK5 (5 µM each/20 µM 3' primer total) |
| 16 µl | IgK cDNA |
| 8 µl | Platinum Taq Hi Fi |
| 640 µl | dd water |
| 100 µl/rxn | |

-continued

PCR program- 1. 94° C. 2 minutes
2. 94° C. 30 seconds
3. 55° C. 30 seconds
4. 68° C. 30 seconds
5. repeat step 2 for 39 times
6. 68° C. 5 minutes
7. 4° C. hold Reactions were purified on 1% GTG Agarose gels. Bands of the correct size, about 400 bp, were purified using a Qiaquick Gel Extraction kit. 0.4 mg of DNA containing agarose was used per spin column. Samples were eluted with 50 µl of EB pre-heated to 55° C. Like samples were pooled and $A_{260/280}$ determined using a Nanodrop spectrophotometer (Nanodrop Technologies, Wilmington, Del.).

Example 4

Generation of VH/VK scFv

VH/VK scFv were generated by Splicing by Overlapping Extension (SOE) PCR. VH For and VK Back primers have shared homology that generate the (Gly$_4$Ser)$_3$ linker (SEQ ID NO: 11) which connects the VH and VL regions to generate the scFv molecule. Reactions were set up as follows:

24 rxns at 100 µl/rxn (VH10/VK assembly as an example)

| | |
|---|---|
| 240 µl | 10x Plat Taq Hi Fi Buffer |
| 24 µl | dNTPs (10 mM) |
| 96 µl | MgSO4 (50 mM) |
| 24 µl | scFv Rev (20 µM) |
| 24 µl | scFv For (20 µM) |
| 141 µl | VH10back (24 pmol of VH/1 pmol per 100 µl rxn) |
| 72 µl | equimolar mix VK1, 2, 9, and 12 DNA (24 pmol total/0.25 pmol each VK per 100 µl rxn) |
| 24 µl | Platinum Taq HiFi |
| 1755 µl | dd water |
| 100 µl/rxn | |

PCR program- 1. 94° C. 2 minutes
2. 94° C. 30 seconds
3. 55° C. 30 seconds
4. 68° C. 1 minutes
5. Go to Step 2 39x
6. 68° C. 5 minutes
7. 4° C. hold scFv bands (about 800 bp) were gel purified as above for VH or VK gel fragments. Like samples were pooled for use in SOE PCR with pYD5'300 bp fragment.

To ensure increased transformation efficiencies we engineered insert DNA fragments that have about 300 bp of homology 5' of the scFv insertion site (SfiI) in the pYD vector. To add this homology to the Human Spleen scFv a primer complimentary to the region immediately upstream of the pYD1sTev SfiI site was designed (pYD5prev). This primer was used in combination with pYD1 5' primer (5107) to generate an about 300 bp fragment to be added to the existing spleen scFv by SOE PCR.

5107/pYD5prev PCR

| | |
|---|---|
| 1 µl | pYDsTev (10 ng/µl) |
| 10 µl | 10x Plat Taq Hi Fi Buffer |
| 4 µl | MgSO4 (50 mM) |
| 1 µl | dNTPs (10 mM) |
| 1 µl | 5107 (20 µM) |
| 1 µl | pYD5prev (20 µM) |
| 1 µl | Platinum Taq Hi Fi |
| 80 µl | dd water |
| 100 µl/rxn | |

PCR program 1. 94° C. 2 minutes
2. 94° C. 30 seconds
3. 55° C. 30 seconds
4. 68° C. 30 seconds
5. Go to step 2 39x
6. 68° C. 5 minutes
7. 4° C. hold 5107/pYD5prev bands (about 300 bp) were gel purified as above for VH or VK gel fragments. Like samples were pooled for use in SOE PCR with spleen scFvs.

scFv + 300 PCR (16x 100 µl rxn mix)

| | |
|---|---|
| 162 µl | 10x Plat Taq Hi Fi Buffer |
| 16.2 µl | dNTPs (10 mM) |
| 64.8 µl | MgSO4 (50 mM) |
| 16.2 µl | 5107 (20 µM) |
| 16.2 µl | scFv For (20 µM) |
| 32.4 µl | VH/VK scFv DNA |
| 16.2 µl | 5107/pYDprev5 DNA |
| 16.2 µl | Platinum Taq HiFi |
| 1279.8 µl | dd water |
| 100 µl/rxn | |

PCR reactions were performed as for the scFv reaction above. ScFv+300 bp (about 1100 bp) were gel purified as above for VH or VK gel fragments. Like samples were pooled for use in electroporation reactions.

Example 5

Prior Art Yeast Library Transformation Protocol

The following is a prior art yeast transformation protocol. Five ml YPD media is inoculated with an EBY100 colony (freshly streaked on a YPD plate) and grow overnight at 30° C. A 50 ml culture is inoculated in YPD media to an absorbance of 0.1 at 600 nm using the overnight culture and cells grown at 30° C. to an absorbance of about 1.3 to 1.5 at 600 nm for about 6 hours. Cells must be in early to mid-log growth phase. Using cells in late log or stationary phase substantially decreases transformation efficiency. While cells are growing, precipitate DNA for transformation using PelletPaint according to the manufacturer's protocol. Typically, DNA to be put into four electroporation cuvettes, each with 5 mg of insert and 1 mg of cut vector is used to generate a library of about 5×10$^7$. Also a backbone-only control is prepared. DNA is left in pellet form. Insert:backbone ratios can be varied from 5:1 to 1:1 with at least 1 mg backbone per cuvette.

Once cells have reached an absorbance of about 1.3-1.5 at 600 nm, 500 µl Tris-DTT buffer is added to the culture and incubated in a shaker at 30° C. for 15 minutes. Transformation efficiency is relatively constant for DTT incubation times of 10-20 minutes, but decreases considerably for incubation over 20 minutes. Cells are pelleted at 2,500 g for 3 minutes at 4° C. and washed with 25 ml ice-cold E buffer (10 mM Tris pH 7.5, 270 mM Sucrose, 1 mM $MgCl_2$) (e.g., rinsed, repelleted and supernatant aspirated). Cells are washed again with 1 ml ice-cold E buffer and resuspended in E buffer to a total volume of 300 μl. DNA control pellets are resuspended in an appropriate volume of cell suspension (50 μl per cuvette). Cells are kept on ice. 50 μl of resuspended cell-DNA mixture is aliquotted per pre-chilled electroporation cuvette and the electroporation cuvettes kept on ice until pulsed.

Cuvettes are loaded into a gene pulser and electroporated at 0.54 kV and 25 μF without a pulse controller. 1 ml of warm (30° C.) YPD media is immediately added to the cuvette. Typical time constants for electroporation range from about 15 ms to 40 ms without greatly affecting transformation efficiency.

Cells are transferred from pulsed cuvettes to a 15-ml Falcon tube. Each cuvette is washed with an additional 1 ml of YPD media to recover the remaining cells from the cuvette. Cells are shaken for 1 hour at 30° C. Cells are pelleted at 2,500 g for 5 minutes and supernatant removed and resuspended in 10 ml SDCAA media. Serial dilutions are plated on SDCAA plates to determine transformation efficiency. The backbone-only control should have an efficiency of less than 1% that of the backbone-plus-insert transformations. The cell suspension is transferred to a flask with 100-1000 ml SDCAA media plus pen-strep (1:100 dilution) and incubated at 30° C. for 24 to 48 hours. This method was use to generate a $8\times10^7$ library and corresponds to the treatment 7 described in Table 3 with an efficiency of 0.4% compared to the optimized protocol of the invention (see Example 6).

Example 6

Yeast Library Transformation Protocol of the Invention Method 2

The invention provides highly efficient and rapid methods of transforming yeast cells, for example, for the production of yeast cell libraries up to $2\times10^{10}$ in size. Multiple components and conditions including the use of $CaCl_2$, $MgCl_2$, sucrose, sorbitol, lithium acetate, dithiothreitol (DTT), electroporation voltage, DNA input, and cell volume were tested and titrated to identify optimal conditions.

The electroporation protocol of the invention is a variation on the protocols of Suga and Hatakeyama (2003) Curr. Genet. 43:206-211; Neumann et al. (1996) Biophys. J. (1996) 71:868-877; Thompson et al. (1998) Yeast 14:565-571; Becker and Guarente (1991) Methods Enzymol. 194, 182-187; Melihon et al. (1990) Biotechnology 8:223-227; Helmuth et al. (2001) Analytical Biochem. 293:149-152; and the protocol provided in Example 5.

Preparation of Yeast Cells:

S. Cerevisiae were Grown Overnight to Stationary Phase. An aliquot of the culture was inoculated into 100 mL of YPD media to reach $OD_{600}$ Of about 0.3. The cells were grown until $OD_{600}$ reached about 1.6 before collecting by centrifugation. The cell pellet was washed twice with cold water, once with 50 mL electroporation buffer (1 M Sorbitol/1 mM $CaCl_2$), and incubated in 20 mL of 0.1 M LiAc/10 mM DTT at 30° C. for 30 minutes. The cells were washed again with 50 mL electroporation buffer, then suspended in 100-200 μL of the electroporation buffer to reach 1 mL volume. This corresponds to approximately 1 to $10\times10^9$ cells/mL.

Figure 1:
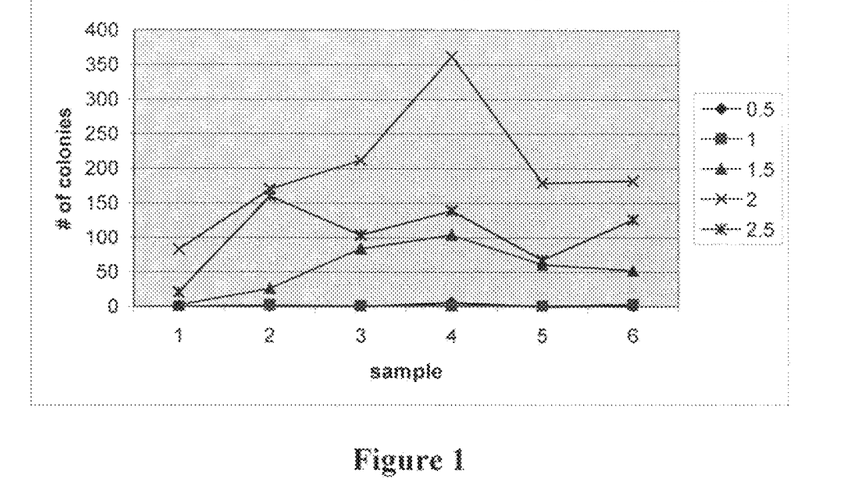
FIG. 1 shows a graphical representation of the data in Table 1, which represents colony count as a function of vector:insert and 2.5 kV/cm to 12.5 kV/cm of voltage.
Figure 2:
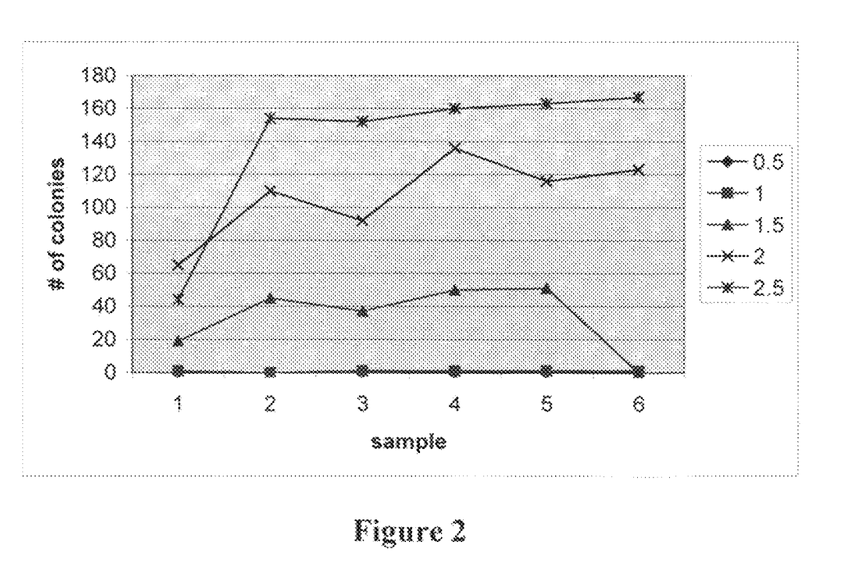
FIG. 2 shows a graphical representation of the data in Table 3, which represents colony count as a function of vector:insert and 2.5 kV/cm to 12.5 kV/cm of voltage.
Figure 3:
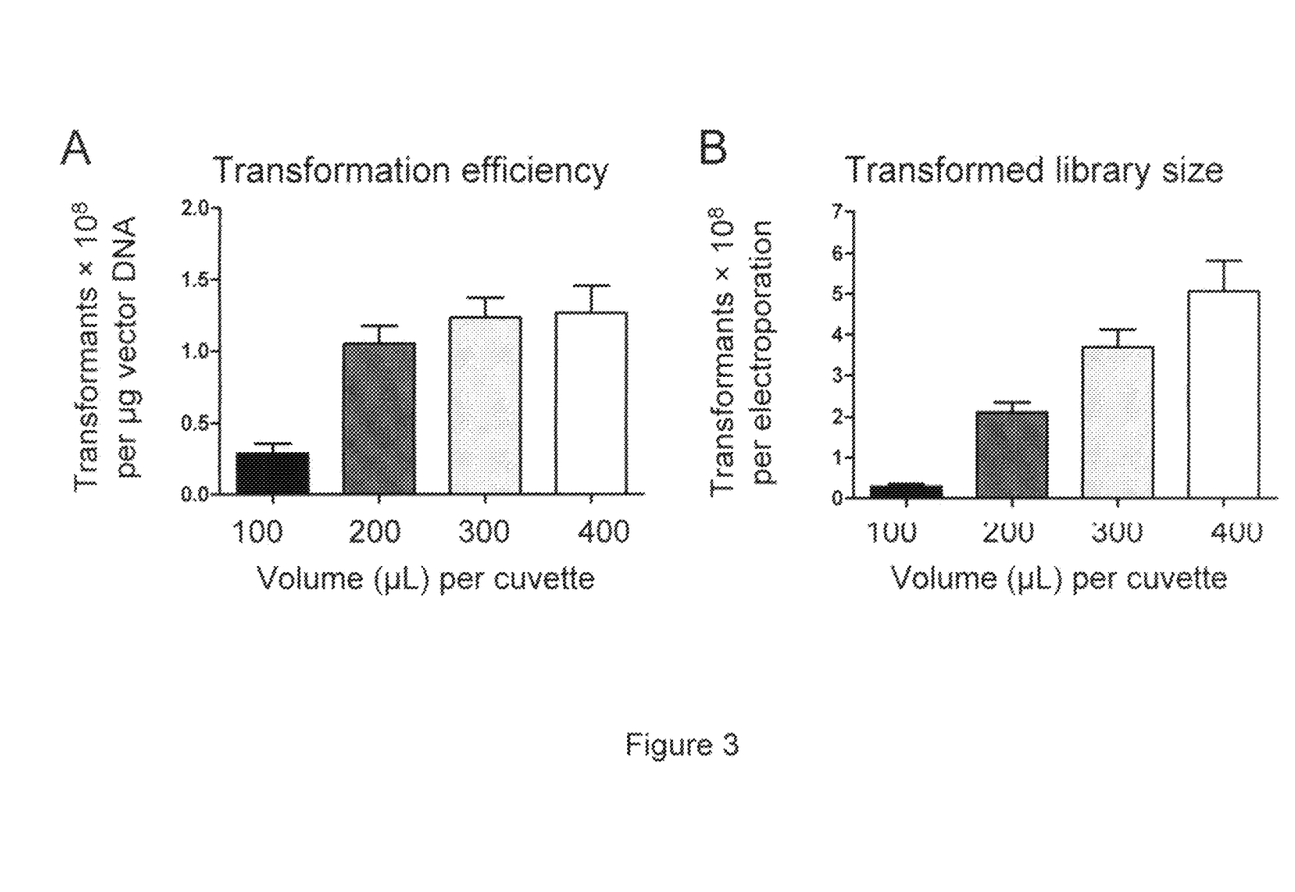
FIG. 3 demonstrates that electroporation efficiency is significantly improved by increasing the volume per cuvette.

Electroporation: 100, 200, 300, or 400 μL of the cell suspension were used for electroporation per cuvette and 1, 2, 3, or 4 μg linearized vector with corresponding 3, 6, 9, or 12 μg DNA insert (vector to insert ratio=1:3) were used. Cells were electroporated at 2.5 kV and 25° F. in a BioRad GenePulser cuvette (0.2 cm electrode gap). Typical electroporation time constant ranged from 3.0 to 4.5 milliseconds. After electroporation, cells were suspended in 10 mL of 1:1 mix of 1 M sorbitol:YPD media and incubated at 30° C. for 1 hour. The cells were then collected and cultured in SD-UT media (-ura, -trp) which contained 20 g/L glucose, 6.7 g/L yeast nitrogen base without amino acids, 5.4 g/L $Na_2HPO_4$, 8.6 g/L $NaH_2PO_4.H_2O$ and 5 g/L casamino acids. The number of transformants was determined by plating 10-fold serial dilutions of transformed cells on selective SD-UT plates. Referring to FIG. 3, 72 hours later the colonies were counted and the transformation efficiencies (A) were expressed as the mean of number of transformants/μg vector DNA±standard deviation; and the yields (B) were expressed as the mean of the total number of transformants per cuvette±standard deviation.

The combination of LiAc, DTT, $CaCl_2$ and sorbitol consistently resulted in a transformation efficiency of $3\pm1\times10^7$ transformants per μg of vector DNA from 1 μg vector DNA and 100 μl yeast cells at a density of $1.6\times10^9$ cells/mL (as determined by optical density at 600 nm, assuming 1 OD equals $10^7$ cells) (FIG. 3). This suggested that roughly 2% of yeast cells were successfully transformed and a $3\pm1\times10^7$ library size can be expected from one electroporation cuvette. To make even larger libraries, the optimal cell volume per individual cuvette was evaluated. Surprisingly, the transformation efficiency was significantly enhanced to $1\times10^8$ transformants per μg vector DNA when the cell volume was increased from 100 μL to 200 μL per cuvette. At the maximal 400 μL cell volume in a 0.2 cm-gap cuvette, library sizes as large as $5\times10^8$ could be easily generated from one cuvette using the same density and cell to DNA ratio (FIG. 3).

This electroporation method is highly reproducible as similar transformation efficiencies were obtained by different operators and on two different electroporators (BioRad Gene Pulser™ model #1652076 and Gene Pulser® II model #1652108).

Example 7

Enhanced Electroporation Efficiencies of S. Cerevisiae by Comparing the Use of LiAc, DTT, Sorbitol, and $CaCl_2$ Table 3 shows electroporation efficiencies, yield per cuvette, % efficiency and maximum library size for the method of Example 7 as well as variations in the method.

TABLE 3

| Treatment | Electroporation efficiency[a] $\times 10^7$ | Yield per cuvette[b] $\times 10^7$ | % of efficiency[c] | Maximal library size[d] |
|---|---|---|---|---|
| 1. Combined protocol | 18.3 ± 2.5 | 73.2 ± 9.7 | 100 | $2 \times 10^{10}$ |
| 2. No LiAc | 1.7 ± 0.1 | 6.7 ± 0.4 | 9 | $1.4 \times 10^9$ |
| 3. No DTT | 0.81 ± 0.017 | 3.3 ± 0.07 | 4 | $8 \times 10^8$ |
| 4. Sorbitol/$MgCl_2$ | 11.4 ± 0.9 | 45.5 ± 3.5 | 62 | $9 \times 10^9$ |

TABLE 3-continued

| Treatment | Electroporation efficiency[a] × 10[7] | Yield per cuvette[b] × 10[7] | % of efficiency[c] | Maximal library size[d] |
|---|---|---|---|---|
| 5. Sorbitol only | 9 ± 1.8 | 36 ± 7.1 | 49 | 8 × 10[9] |
| 6. Sucrose/CaCl$_2$ | 0.4 ± 0.3 | 1.6 ± 1.5 | 2 | 3.8 × 10[8] |
| 7. Sucrose/MgCl$_2$ | 0.09 ± 0.01 | 0.4 ± 0.07 | 0.4 | 8 × 10[7] |

[c]Number of transformants per µg of vector DNA
[d]Total number of transformants per cuvette electroporation reaction
[e]Assuming the transformation efficiency obtained using the protocol equal to 100%
[f]Assuming 25 cuvette electroporation reactions made in one day The combined protocol is that described in Example 7 of an electroporation of 400 µl of yeast suspension (1.6×10$^9$/mL) with 4 µg of vector and 12 µg of DNA insert. For the other treatments, the combined protocol was follow Example 7 except for the following changes: (2) Cells were pre-treated only with DTT; (3) Cells were pre-treated only with LiAc; (4) MgCl$_2$ was used instead of CaCl$_2$. (5) CaCl$_2$ was excluded from electroporation buffer; (6) 270 mM sucrose was used instead of 1M sorbitol; and (7) 270 mM sucrose/1 mM MgCl$_2$ was used as the electroporation buffer.

As shown in Table 2, the elimination of DTT or LiAc pre-treatment resulted in respective efficiency reductions of 93.3% and 85.7%. Similarly, elimination of sorbitol or replacing it by sucrose led to a loss of greater than 96% efficiency (Table 2 and data not shown). This is consistent with the previous findings that the ability of sorbitol to stabilize osmotic pressure and support yeast membrane integrity after electroporation was at least partially responsible for achieving high transformation efficiency (Becker, D. M. and Guarente, L. (1991) *Methods Enzymol.* 194:182-7; Weaver, J. C. et al. (1988) *FEBS Lett.* 229:30-4). The presence of CaCl$_2$ during electroporation, presumably to facilitate DNA binding to cell membrane (Neumann, E. et al. (1996) *Biophys. J.* 71:868-77), appeared to be the least critical parameter as its elimination only modestly decreased the transformation efficiency by 30% and its substitution by MgCl$_2$ only resulted in a small 11% decrease.

Example 8

Effect of Voltage on Electroporation Efficiency

An experiment was performed to determine the effect of voltage on electroporation efficiency and to determine the best vector:insert ratio. The experiment was performed twice. The protocol of Example 2 was performed using several voltages in the range of 0.5-2.5 kV and with several vector:insert ratios in the range of 1:1 to 1:10 (w/w), wherein the amount of vector DNA was kept constant at 1 µg. All reactions were concentrated and precipitated using SureClean and resuspending the DNA pellet in ddH20 before adding the cell suspension, as described above.

In each experiment, yeast cells were prepared as described above. The volume of Vector/Insert was fixed at 11.6 µl for 5 reactions.

Experiment #1

TABLE 4

Graph Depicting Colony Count As A Function Of Vector: Insert And Field Strength[1]

| | 2.5 kV/cm | 5 kV/cm | 7.5 kV/cm | 10 kV/cm | 12.5 kV/cm |
|---|---|---|---|---|---|
| 1:1 | 0 | 0 | 2 | 83 | 21 |
| 1:2 | 0 | 2 | 26 | 170 | 160 |

TABLE 4-continued

Graph Depicting Colony Count As A Function Of Vector: Insert And Field Strength[1]

| | 2.5 kV/cm | 5 kV/cm | 7.5 kV/cm | 10 kV/cm | 12.5 kV/cm |
|---|---|---|---|---|---|
| 1:3 | 0 | 1 | 84 | 212 | 104 |
| 1:4 | 6 | 1 | 104 | 362 | 139 |
| 1:5 | 0 | 1 | 61 | 179 | 68 |
| 1:10 | 0 | 3 | 52 | 182 | 126 |

[1]Electroporations were performed in a 0.2 cm gap cuvette with voltages ranging from 0.5 to 2.5 kV

TABLE 5

Transfection Efficiency As A Function Of Vector: Insert And Field Strength[1]

| Trans efficiency | 7.5 kV/cm | 10 kV/cm | 12.5 kV/cm |
|---|---|---|---|
| 1:1 | 2.00E+06 | 8.30E+07 | 2.10E+07 |
| 1:2 | 2.60E+07 | 1.70E+08 | 1.60E+08 |
| 1:3 | 8.40E+07 | 2.12E+08 | 1.04E+08 |
| 1:4 | 1.04E+08 | 3.62E+08 | 1.39E+08 |
| 1:5 | 6.10E+07 | 1.79E+08 | 6.80E+07 |
| 1:10 | 5.20E+07 | 1.82E+08 | 1.26E+08 |

[1]Electroporations were performed in a 0.2 cm gap cuvette with voltages ranging from 0.5 to 2.5 kV Results: Transformation was detected with a 1:1 vector:insert ratio in the voltage range of 1.5 to 2.5; with a 1:2 vector:insert ratio in the voltage range of 1.0 to 2.5; 1:3 vector:insert ratio in the voltage range of 1.0 to 2.5; 1:4 vector:insert ratio in the voltage range of 0.5 to 2.5; 1:5 vector:insert ratio in the voltage range of 1.0 to 2.5; and 1:10 vector:insert ratio in the voltage range of 1.0 to 2.5. For all vector:insert ratios, peak colony count was achieved using a voltage of 2.0 kV. Optimal conditions appeared to be a vector:insert ratio of 1:4 and a voltage of 2.0 kV, where a transfection efficiency of 3.62×10$^8$ was achieved.

Experiment #2

TABLE 6

Graph Depicting Colony Count As A Function Of Vector: Insert And Field Strength[1]

| Data set 2 | 2.5 kV/cm | 5 kV/cm | 7.5 kV/cm | 10 kV/cm | 12.5 kV/cm |
|---|---|---|---|---|---|
| 1:1 | 0 | 1 | 19 | 65 | 44 |
| 1:2 | 0 | 0 | 45 | 110 | 154 |
| 1:3 | 0 | 1 | 37 | 92 | 152 |
| 1:4 | 0 | 1 | 50 | 136 | 160 |
| 1:5 | 0 | 1 | 51 | 116 | 163 |
| 1:10 | 0 | 1 | 0 | 123 | 167 |

[1]Electroporations were performed in a 0.2 cm gap cuvette with voltages ranging from 0.5 to 2.5 kV

TABLE 7

Transfection Efficiency As A Function
Of Vector: Insert And Field Strength[1]

| Trans efficiency | 7.5 kV/cm | 10 kV/cm | 12.5 kV/cm |
|---|---|---|---|
| 1:1 | 1.90E+07 | 6.50E+07 | 4.40E+07 |
| 1:2 | 4.50E+07 | 1.10E+08 | 1.54E+08 |
| 1:3 | 3.70E+07 | 9.20E+07 | 1.52E+08 |
| 1:4 | 5.00E+07 | 1.36E+08 | 1.60E+08 |
| 1:5 | 5.10E+07 | 1.16E+08 | 1.63E+08 |
| 1:10 | 0.00E+00 | 1.23E+08 | 1.67E+08 |

[1] Electroporations were performed in a 0.2 cm gap cuvette with voltages ranging from 0.5 to 2.5 kV Results: Transformation was detected with a 1:1 vector: insert ratio in the voltage range of 1.0 to 2.5; with a 1:2 vector:insert ratio in the voltage range of 1.5 to 2.5; 1:3 vector:insert ratio in the voltage range of 1.0 to 2.5; 1:4 vector:insert ratio in the voltage range of 0.5 to 2.5; 1:5 vector:insert ratio in the voltage range of 1.0 to 2.5; and 1:10 vector:insert ratio in the voltage range of 1.0 to 2.5, with no colonies at 1.5 kV. For vector:insert ratio 1:1 peak colony count was achieved using a voltage of 2.0 kV. For all other vector:insert ratios a 2.5 kV voltage was optimal. Optimal conditions appeared to be a vector:insert ratio of 1:10 and a voltage of 2.5 kV. The results of this experiment indicate that an optimal voltage is 2-2.5 kV, with the increased amounts of insert relative to vector not providing a significant advantage over a ratio of 1:2.

Experiment #3

Figure 4:
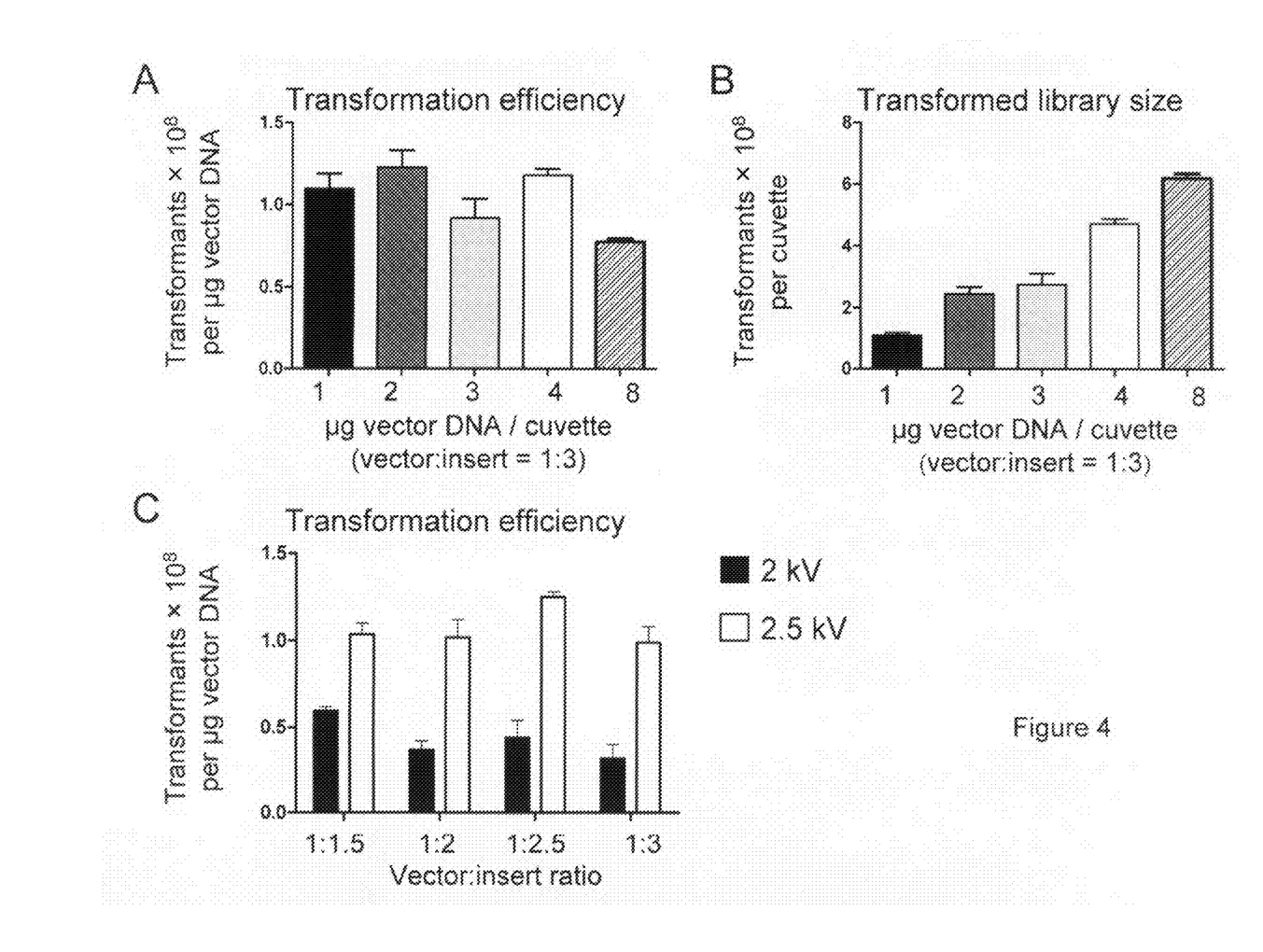
FIG. 4 demonstrates that increased DNA input and high voltage, but not vector to insert ratio, are critical for maximal transformation efficiency.

Increased DNA Input and High Voltage, but not Vector to Insert Ratio are Critical for Maximal Transformation Efficiency The effect of DNA quantity on transformation efficiency was examined by electroporating 400 μL yeast suspension with 1, 2, 3, 4, or 8 μg of vector DNA while maintaining the same 1:3 vector to insert ratio. *S. cerevisiae* were treated as described in Example 7. A 400 μL yeast cell suspension ($1.6 \times 10^9$ cells/mL) was electroporated using 1, 2, 3, or 4 μg vector per cuvette (while maintaining a vector to insert ratio=1:3). Referring to FIG. 4, after 72 hours the number of colonies was determined and represented as (A) transformation efficiency (average transformants per μg of vector DNA±standard deviation) and (B) transformation yield (total number of transformants per cuvette±standard deviation). Additionally, (C) 400 μL yeast suspension was electroporated by 2 or 2.5 kV and different vector to insert DNA ratios. The transformation efficiencies are expressed as average transformants per μg of vector DNA.

Interestingly, the transformation efficiency did not significantly change when up to 4 μg vector DNA was used for each transformation and only slightly decreased with 8 μg vector DNA input (FIG. 4A). As expected, the yield of the transformed library size correspondingly increased with increasing amounts of DNA input (FIG. 4B). Overall, the use of 4 μg linearized vector turned out to be the most convenient and efficient condition. To explore whether the 12 μg DNA insert (to achieve a vector to insert ratio of 1:3) can be reduced, different vector to insert ratio were tested. Results show that the ratio can be as low as 1:1.5 without negatively impacting the transformation efficiency (FIG. 4C). However, lower transformation efficiencies were observed when the vector to insert ratio was below 1:1 or above 1:5 (data not shown). In addition, the electroporation voltage setting was found to be critical as reduction of electroporation voltage from 2.5 kV to 2 kV or lower resulted in a significant loss of transformation efficiency (FIG. 4C and data not shown).

Example 9

Naïve Human Spleen Antibody Library Diversity And Productivity

The electroporation protocol of the invention was used to generate a large human antibody library. Human VH and VK cDNA fragments from commercially available spleen poly-A RNA were separately amplified using polymerase chain reactions (PCR) and previously reported primers (Sblattero, D. and Bradbury, A. (1998) *Immunotechnology* 3:271-8). The VK fragments were proportionally pooled together such that each germline family would be equally represented in the library. ScFv fragments were separately prepared from VH and pooled VK fragments by overlapping PCR. Multiple yeast libraries were generated from these scFv fragments mixed with linear vector DNA by electroporation and proportionally pooled together to maintain equal representations of all VH germline sequences. A large number of yeast colonies were sequenced to analyze the scFv germline composition and the results confirmed a high diversity. With the exception of the rare VH7 germline genes all the other germline gene families were identified and their representations were roughly proportional to their germline gene numbers in our library (see Table 8). Since no identical VH sequences were identified, it is estimated that the library diversity has a 95% probability to be as large as 1012, assuming a maximal theoretical diversity of $10^4$ for VK and a diversity of $10^8$ for VH (about $10^8$ donor B cells) and is only limited by the library size. By using this highly efficient yeast electroporation protocol it is now possible to construct yeast libraries with sizes approaching those of typical phage libraries (Hoogenboom, H. R. (2002) *Methods Mol. Biol.* 178:1-37; Sblattero, D. and Bradbury, A. (2000) *Nat. Biotechnol.* 18:75-80). Indeed, it took only one day to generate a $2 \times 10^{10}$ yeast library simply by scaling up the electroporation to twenty cuvettes, and $10^9$ yeast libraries are now routinely made for affinity maturation or other optimization purposes.

TABLE 8

Naïve Human spleen antibody library diversity

| VH Germline Families | Theoretical distribution (%) | Naïve Human spleen library observed distribution (%) (n = 347) |
|---|---|---|
| VH1 | 21 | 15 |
| VH2 | 7 | 5 |
| VH3 | 50 | 62 |
| VH4 | 16 | 16 |
| VH4 (DP63) | 2.5 | 3.2 |
| VH5 | 0.5 | 0.3 |
| VH6 | 2.5 | 1.5 |
| VH7 | 0.5 | 0 |

To demonstrate that the constructed libraries produce antibodies with reasonably good affinity, the human spleen antibody library was selected against human tumor necrosis factor α (TNFα) initially by magnetic activated cell sorting to reduce the library size to about $10^7$ cells, followed by multiple rounds of FACS essentially as previously described (Chao, G. et al. (2006) *Nat. Protoc.* 1:755-68; Feldhaus, M. J. et al. (2003) *Nat. Biotechnol.* 21:163-70). Multiple binders to TNFα were identified and their VH are derived from VH1, VH3 and VH4 and Vκ from Vκ1 and Vκ2 human germline sequences, indicating that the library indeed produced antigen binders from a diverse antibody pool. One of the scFv showed a 4 nM affinity and another showed a 40 nM affinity to TNFα. Upon IgG conversion the 4 nM binder maintained a similar binding affinity (1.5 nM by ELISA), while the 40 nM binder showed a significant increase in affinity (0.3 nM by ELISA). This increase in apparent affinity could be due to the avidity of the converted IgG interacting with two TNFα in the same homotrimeric TNFα protein. Additional library selections have also identified low nanomolar affinity antibodies to human IL-18 from this library (data not shown).

By using the most optimal electroporation condition, one can routinely achieve yeast transformation efficiency of $1 \times 10^8$ yeast transformants/μg vector DNA. As this transformation efficiency is achieved in minimal cell volume (100 μl), it is highly amenable to automation and multiwell electroporation devices. For instance, one can envision that by setting up the electroporation in a 96-well electroporation plate, a library size of $9.6 \times 10^9$ can be achieved. When this multiwell electroporation is repeated 10 to 11 times manually or by automation, one can easily construct a yeast library of greater than $10^{11}$ transformants in one day. This efficiency and possible size of constructed library is approaching that of a typical phage library, and is highly desirable in maximizing the success rate of using the constructed yeast library for the various applications one can apply to the library, such as yeast antibody display and yeast two hybrid interaction screening.

REFERENCES

1. Chao, G. et al. (2006) *Nat. Protoc.* 1:755-68.
2. Gai, S. A. and Wittrup, K. D. (2007) *Curr. Opin. Struct. Biol.* 17:467-73.
3. Griffiths, A. D. et al. (1994) *EMBO J.* 13:3245-60.
4. He, M. and Khan, F. (2005) *Expert Rev. Proteomics* 2:421-30.
5. Hoogenboom, H. R. (2002) *Methods Mol. Biol.* 178:1-37.
6. Hoogenboom, H. R. (2005) *Nat. Biotechnol.* 23:1105-16.
7. Hoet, R. M. et al. (2005) *Nat. Biotechnol.* 23:344-8.
8. Rothe, C. et al. (2008) *J. Mol. Biol.* 376:1182-200.
9. Lee, H. W. et al. (2006) *Biochem. Biophys. Res. Commun.* 346:896-903.
10. Lipovsek, D. et al. (2007) *J. Mol. Biol.* 368:1024-41.
11. Segal, L. et al. (2007) *Bioinformatics* 23:1440-9.
12. Becker, D. M. and Guarente, L. (1991) *Methods Enzymol.* 194:182-7.
13. Helmuth, M. et al. (2001) *Anal. Biochem.* 293:149-52.
14. Neumann, E. et al. (1996) *Biophys. J* 71:868-77.
15. Simon, J. R. (1993) *Methods Enzymol.* 217:478-83.
16. Suga, M. and Hatakeyama, T. (2003) *Curr. Genet.* 43:206-11.
17. Thompson, J. R. et al. (1998) *Yeast* 14:565-71.
18. Gietz, R. D. et al. (1995) *Yeast* 11:355-60.
19. Brzobohaty, B. and Kovac, L. (1986) *J. Gen. Microbiol.* 132:3089-93.
20. Weaver, J. C. et al. (1988) *FEBS Lett.* 229:30-4.
21. Sblattero, D. and Bradbury, A. (1998) *Immunotechnology* 3:271-8.
22. Sblattero, D. and Bradbury, A. (2000) *Nat. Biotechnol.* 18:75-80.
23. Feldhaus, M. J. et al. (2003) *Nat. Biotechnol.* 21:163-70.

INCORPORATION BY REFERENCE

The contents of all cited references (including literature references, patents, patent applications, and web sites) that may be cited throughout this application are hereby expressly incorporated by reference. The practice of the invention will employ, unless otherwise indicated, conventional techniques of cellular electroporation and yeast cell biology, which are well known in the art.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

The invention claimed is:

1. A method of preparing a yeast library by electroporation of yeast cells comprising the steps of:
   incubating the yeast cells in a solution comprising 0.01 to 1.0 M lithium acetate (LiAc) and 1 to 100 mM dithiothreitol (DTT),
   providing a suspension comprising vector DNA, insert DNA, the incubated yeast cells, 0.1 to 10 M sorbitol, and 0.1 to 10 mM $CaCl_2$ or $MgCl_2$, and
   electroporating the suspension at 5 kV/cm to 12.5 kV/cm with a capacitance of about 10 to about 50 μF;
   wherein the yeast cells are transformed with a transformation efficiency greater than $1 \times 10^8$ transformed yeast cells per μg of nucleic acid vector, thereby to obtain a library size of at least $1 \times 10^9$.

2. The method of claim 1, wherein the suspension comprises 1M sorbitol and 1 mM $CaCl_2$.

3. The method of claim 1, wherein the suspension comprises 1M sorbitol and 1 mM $MgCl_2$.

4. The method of claim 1, wherein the yeast cells are incubated in a volume comprising cold 0.1M LiAc and 10 mM DTT.

5. The method of claim 1, wherein the suspension is electroporated at 12.5 kV/cm with a capacitance of about 25 μF.

6. The method of claim 1, wherein the electroporating step is performed in a 0.2 cm gap cuvette.

7. The method of claim 1, wherein 1 μg to 8 μg of vector DNA is used.

8. The method of claim 1, wherein 4 μg of vector DNA is used.

9. The method of claim 1, wherein the vector is linear.

10. The method of claim 1, wherein the suspension comprises 400 μl of $1.6 \times 10^9$ yeast cells/mL.

11. The method of claim 1, wherein the ratio of vector DNA to insert DNA is in the range of 1:0.5 to 1:10.

12. The method of claim 1, wherein the ratio of vector DNA to insert DNA is 1:3.

13. A method for transforming yeast with DNA to prepare a library comprising the steps of:
   culturing yeast cells to an $OD_{600}$ of about 1.0 to about 2;
   washing the yeast cells in water;
   washing the yeast cells in a first solution comprising sorbitol and $CaCl_2$;
   incubating the yeast cells in a second solution comprising 0.01 to 1.0 M lithium acetate (LiAc) and 1 to 100 mM dithiothreitol (DTT);
   washing the yeast cells in a third solution comprising sorbitol and $CaCl_2$;
   resuspending the yeast cells in a fourth solution comprising 0.1 to 10 M sorbitol and 0.1 to 10 mM $CaCl_2$ or $MgCl_2$ to form a yeast cell electroporation suspension;
   adding a volume of the yeast cell electroporation suspension to vector DNA and insert DNA to form a yeast cell—DNA electroporation suspension; and
   electroporating the yeast cell—DNA electroporation suspension at a voltage of between about 5 kV/cm and about 12.5 kV/cm in a 0.2 cm gap cuvette,
   wherein the yeast cells are transformed with a transformation efficiency greater than $1 \times 10^8$ transformed yeast cells per μg of nucleic acid vector, thereby to obtain a library size of at least $1 \times 10^9$.

14. The method of claim 1, wherein the yeast belongs to species *Saccharomyces cerevisiae*.

15. The method of claim 13, wherein the yeast belongs to species *Saccharomyces cerevisiae*.

* * * * *

SEQUENCE LISTING

<160> NUMBER OF SEQ ID NOS: 11

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tccaccttcc actg                                                     14

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

```
caggcacaca acag                                                         14

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gagtgtcaca gagc                                                         14

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agttccacga cacc                                                         14

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaaggtgtgc acg                                                          13

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccacgctgct gag                                                          13

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
actttgcaca ccac                                                         14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tttgttgccg ttgg                                                         14
```

```
<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gggaattctc acagg                                                    15

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcgccctgaa aatacaggtt ttc                                           23

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Gly Ser Gly Gly Gly Gly Ser
1               5                   10                  15
```